Figure 1:
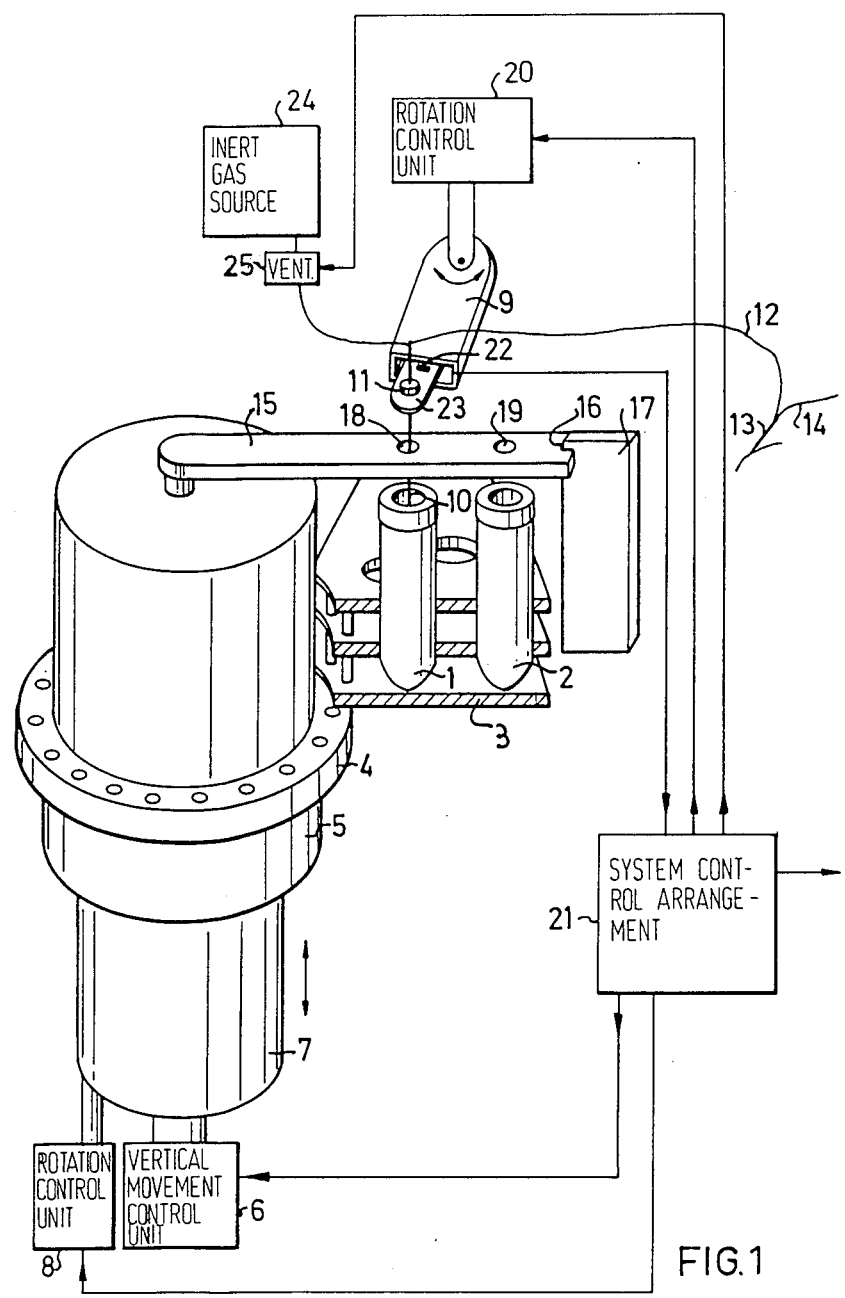

United States Patent [19]

Backlund et al.

[11] Patent Number: 4,715,413

[45] Date of Patent: Dec. 29, 1987

[54] APPARATUS FOR MANIPULATING SMALL VOLUMES OF LIQUID

[76] Inventors: Ulf E. H. H. Backlund, Tolvmansvägen 27, S-191 71 Sollentuna; Carl U. Ungerstedt, Mjölnarstigen 11, S-181 46 Lidingö, both of Sweden

[21] Appl. No.: 916,634

[22] Filed: Oct. 8, 1986

[30] Foreign Application Priority Data

Oct. 18, 1985 [SE] Sweden ................................ 8504910

[51] Int. Cl.⁴ ................................................ B65B 3/04
[52] U.S. Cl. ...................................... 141/94; 141/374; 73/864.24; 422/100
[58] Field of Search ..................... 141/374, 94, 95, 96, 141/1-12; 422/57, 71, 100, 99, 102, 104; 73/864.24, 864.25

[56] References Cited

U.S. PATENT DOCUMENTS 4,286,637  9/1981  Wilson ................................. 141/374

Primary Examiner—Houston S. Bell, Jr.
Attorney, Agent, or Firm—Young & Thompson

[57] ABSTRACT

The invention relates to apparatus for manipulating small quantities of liquid, comprising at least one test tube for accommodating the quantity of liquid, a cannula which can be inserted into the vessel, and a control arrangement for controlling the system vessel and cannula in relation to one another in a manner such as to bring the cannula to the bottom of the vessel. In accordance with the invention, the cannula is provided with a suspension structure which is connected to a mechanical or electronic sensor arrangement which records pressure acting axially on the end of the cannula. When pressure is detected, the control arrangement halts further insertion of the cannula into the vessel.

7 Claims, 3 Drawing Figures

APPARATUS FOR MANIPULATING SMALL VOLUMES OF LIQUID

The present invention relates to apparatus for manipulating small volumes of liquid.

Apparatus for collecting small volumes of liquid is known, in which the liquid to be collected is dripped through a cannula into a collecting tube. When the required volume of liquid has been collected in a particular tube, the cannula is moved to the next tube in sequence, or conversely the tubes are moved in relation to the cannula, so that the cannula is able to deliver liquid to the next tube.

Developments in analytical chemistry have progressed more and more towards microchemical methods with the use of minute quantities of liquid. This applies, for example, to the field of liquid chromatography in which the collection of fractions subsequent to chromatographic separation requires the manipulation of minute quantities of liquid, particularly in conjunction with so-called microbore techniques. In this particular methodology the diameter of the separation column decreases radically, with the flow of the mobile phase decreasing to a corresponding extent, i.e. the flow decreases from milliliters per minute to micromilliliters per minute.

This has a number of consequences when manipulating liquid quantities in conjunction with the process of collecting fractions and automatically injecting the fractions into the chromatographic system. Because of the slow rate of flow, a fraction may be smaller than a falling droplet. If the fraction volume is greater, a droplet may nevertheless represent such a large proportion of the fraction as to loose the necessary precision in the division into fractions if the droplet falls into a bordering tube.

Microbore technology is often employed in the analysis of minute sample quantities, since in chromatography the injection volume is often restricted to 0.1–1 microliters. The manipulation of minute sample volumes places particular requirements on autoinjectors. These are used to withdraw the sample by suction from tubes placed in a sample turntable or like arrangement. The sample is then conveyed to an injection valve, by withdrawing the sample into the valve by suction, or by placing the cannula automatically into the injection hole of the valve.

The use of progressively finer sample tubes, or test tubes, has been initiated in order to enable very small quantities of liquid to be manipulated, these tubes often being provided with a conical bottom. It is difficult with tubes of this kind, however, to place the suction cannula in the close proximity of the bottom of the tube so as to enable the largest possible quantity of liquid to be withdrawn.

Minute volumes of liquid are also used in conjunction with automatic pipetting machines, in addition to liquid chromatography, these machines being used for preparing samples, wherein reagent and sample are mixed together in various ways. The problems of reaching down to the bottom of the respective test tubes, so as to be able to use the smallest possible amount of sample, is also encountered in these processes however.

A further complication encountered in conjunction with the manipulation of minute liquid quantities and with the development of sensitive or delicate analytical methods is one which involves the risk of substances, primarily biological substances, escaping from the system during the automatic manipulation of the sample. This risk is counteracted by using chilled samples and by shielding the samples with impervious membranes. In some cases the air located inwardly of the impervious, or tightly sealing, membrane placed over the mouth of the test tube may be replaced with an inert gas.

The problem of manipulating minute volumes of liquid is normally solved by causing the end of the cannula used to touch the wall of the test tube. The advantage here is that the tip of the cannula is able to slide along the wall of the test tube without striking the bottom of the tube. One drawback, however, is that a droplet may remain seated on the wall of the tube, without reaching the tube bottom, and be withdrawn from the tube during a subsequent sample withdrawing process. In certain cases, it may also be necessary to include initially a small amount of acid in the tube, in order to prevent further degradation of the sample. This acid lies in droplet form on the tube bottom, and in the aforesaid respect there is the risk that a droplet which is located on the wall of a tube may not run down into the acid.

Another method often applied in practice is one in which the cannula is caused to touch the bottom of the sample tube or test tube. Adjustments to the movements of the cannula have previously been made either by programming the vertical movements of the cannula or the test tube, depending on which can be moved in relation to the other to a given terminal point in space, or by mounting the tube on a resilient suspension which enables the cannula to be brought to the bottom of the tube without risk of damaging the cannula or the tube.

Arrangements of this kind, however, are expensive, since it is necessary to fit each test tube with a separate coil-spring suspension. In addition, with such arrangements the tip of the cannula may become blocked when contacting the bottom of the tube. For this reason tubes having laterally oriented openings are often used, although such tubes greatly restrict the possibility of withdrawing liquid which is located in the deepest region of the tip of the tube in conjunction with autoinjection processes. In conjunction with fraction collecting processes, there is also the risk of a droplet remaining on the cannula wall.

The aforementioned problems are solved in a simple, reliable and inexpensive manner with apparatus described in detail below.

The invention offers a general solution to the problem of withdrawing by suction and of depositing minute quantities of liquid in conjunction with autoinjection processes, fraction collecting processes, and automatic pipetting processes. According to the invention the cannula is provided with a physical suspension means which is connected to a mechanical or electronic sensor arrangement adapted to register pressure acting against the end of the cannula in the axial direction thereof. This arrangement can be given different forms, depending upon application and upon manufacturing costs. The use of a sensor enables the position at which the tip of the cannula reaches the bottom of the tube to be precisely determined, thereby eliminating the need to provide each cannula with the coil-spring suspension used hitherto. In addition, the use of a sensor enables the tip of the cannula to be moved out of direct contact with the bottom of the tube in a controlled fashion. The distance between the tip of the cannula and the bottom of the tube can be kept very small according to the manner in which the movement of the cannula or the tube is controlled. It is important that this movement is sufficiently small to ensure that the distance to the bottom of the tube is smaller than the diameter of the droplet which forms at the upper end of the cannula when liquid flows out.

The invention has a general application in conjunction with collecting small fractions, the autoinjection of small samples, and the pipetting of small volumes. The invention enables the free end of a pipette tube to be positioned exactly, irrespective of the depth of the test tube used, thereby enabling tubes of varying dimensions to be used in conjunction with automatically functioning apparatus. The method according to the invention also has an advantage over the method in which the mouth of the cannula is located with the aid of a space coordinate system, since this latter method does not take into account the fact that the bottoms of mutually different sample tubes produced in a single manufacturing series normally vary in thickness.

Figure 2:
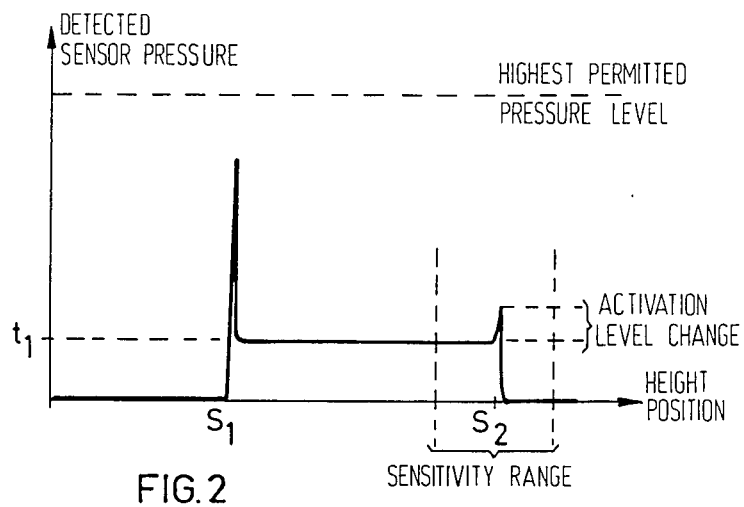
Figure 3:
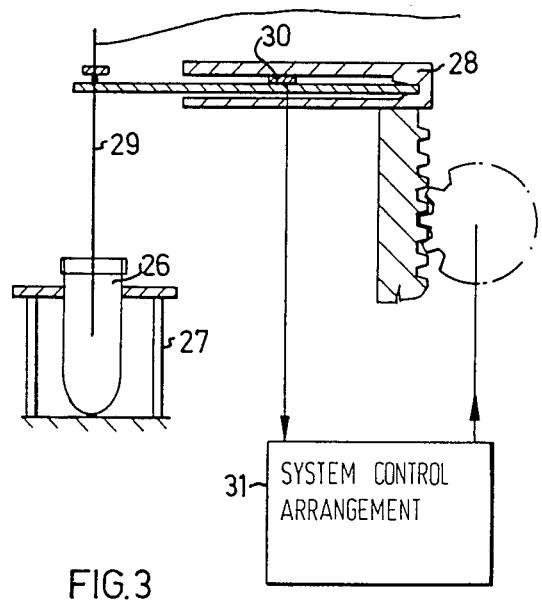

The invention will now be described in more detail with reference to the accompanying drawings, in which FIG. 1 is a schematic illustration, partly in perspective, of an embodiment of the arrangement according to the invention;

FIG. 2 is a diagram of a sensor signal as a function of height of a part of the arrangement in FIG. 1; and FIG. 3 is a schematic illustration of a further embodiment of the arrangement according to the invention.

In the embodiment illustrated in FIG. 1, test tubes 1, 2 are placed in an arcuate holder 3 capable of accommodating a plurality of tubes, of which only two are shown for the sake of illustration. The holder 3, which is shown partially cut away, is detachably secured (by securing means not shown) to an annular, outwardly projecting shoulder 4 located on a cylinder 5. The cylinder 5 is controlled by a vertical movement control unit 6 for vertical telescopic movement upwardly and downwardly over and around a further cylinder 7 of smaller diameter than the cylinder 6. Movement of the cylinder 5 can be controlled in a number of different ways, none of which will be described in detail since they form no part of the present invention.

Although the illustrated arrangement according to the invention is envisaged for use in collecting a sample from a patient or corresponding subject, it will be appreciated that the illustrated arrangement can also be used when a sample is to be collected from a sample tube with the aid of a cannula, as made more apparent hereinafter.

Arranged above the holder 3 carrying the tubes 1,2 is a further holder 9 which carries a cannula 10 attached to a cannula attachment 11. For the purpose of collecting sample liquid, the cannula 10 is connected, via a flexible elastic hose 12, to a sampling needle 13 inserted into the subject from which a sample is to be taken. The needle 13 is of a particular kind that is capable of extracting those substances to be examined, and accordingly is provided with an extraction hose 14 which is connected to a liquid source. Since this needle arrangement forms no part of the invention it will not be described in more detail here.

Rotatably mounted on the shaft of the cylinder 5 is a bar 15, the function of which is to hold the tubes 1, 2 in place when the cannula 10 is subsequently withdrawn from the tubes. The end of the bar 15 remote from the aforesaid shaft has a groove 16 provided therein. The groove 16 accommodates a firmly secured guide 17, this arrangement being such that the bar 15 will always have the same orientation irrespective of the vertical position of the cylinder 5. The bar 5 has provided therein a hole 18 and a hole 19, each of which is positioned immediately above the location of a respective tube 1,2.

When the cylinder is in its lowered position and the cannula 10 is located above the bar 15, the cannula holder 9 can be rotated by a rotation control unit 20, so that the cannula can be inserted alternately into a radially inner tube 1 or a radially outer tube 2. Similarly, when occupying its lowered position the cylinder 5 itself can be rotated by means of a rotation control unit 8, so as to bring a further pair of test tubes beneath the bar 15.

A master control arrangement 21 for controlling the system as a whole is constructed or programmed to cause, in sequence, the vertical control unit 6 to move the cylinder 5 together with the tube holder 3 and the bar 15 to the aforesaid lower position, so that the tip of the cannula 10 is located above the bar 15, to cause the rotation control unit 2 to change the position of the cannula attachment 11 above the other of the holes 18,19, to cause the rotation control unit 8, each alternate time, to rotate the cylinder in order to bring two further tubes into position beneath the bar 15, and to cause the control unit 6 to move the cylinder 5 to move upwards. It is also possible to have some some or combination control of the angular and the vertical movements of the cylinder 5 such that the angular rotation of the cylinder 5 is performed automatically when it is in its aforesaid lower position without the need of having a particular rotation control unit 8. The most important feature of the invention, however, is that the cannula holder 9 is provided with a sensor 22 effective for detecting any upward movement to which the cannula attachment 11 may be subjected subsequent to inserting the cannula 10 into a test tube, i.e. upward movement resulting from contact of the tip of the cannula with a resisting obstacle in the tube. The sensor 22 itself is illustrated solely in FIG. 1, since the type of sensor used is relatively unimportant to the present invention. Pressure sensors of the piezoelectric capacitive, electromagnetic or magnetostrictive type can be used. In order to facilitate detection of the aforesaid pressure, the cannula holder 9 of the FIG. 1 embodiment has the form of a sleeve. The cannula attachment 11 is placed on the outwardly projecting part of a tongue 23 which extends partially into the sleeve 9. The sensor 22 is preferably placed between the upper side of the tongue 23 and the upper wall of the sleeve 9. Suitably, the tongue 23 is resiliently mounted in the sleeve 9, preferably at the rear thereof. When the sensor 22 signals that the cannula has reached the bottom of a test tube, upward movement of the cylinder 5 is stopped by the vertical movement control unit 6, in response to a signal from the master control arrangement 21. As beforementioned, the control arrangement 21 can then instruct the vertical movement control unit 6 to lower the cylinder 5 very slightly, so that the cannula is no longer in direct contact with the bottom of the tube, but is spaced therefrom at a distance not smaller than the diameter of the droplet which forms at the upper end of the cannula when liquid flows out.

The sensor 22 may be a linear type sensor, although a higher degree of sensitivity is obtained when, for example, a quadratic or an exponential type of sensor is used.

The mouths of the test tubes 1, 2 are often covered with a protective membrane, which must be perforated by the cannula when delivering liquid to or removing liquid from the test tube. This membrane resists the passage of the cannula as it enters the test tube. When the initial resistance is detected, however, the position of the cylinder 5 in its upward movement path is far removed from the position at which the cannula can be expected to be located when in contact with the bottom of a test tube. Consequently, the control arrangement may be constructed to react or to respond solely to signals transmitted by the sensor when the vertical height position of the cylinder 5 lies within a given height range, a so-called sensitivity range.

It is possible, however, for a test tube to be positioned obliquely in its holder, or for the operator to forget to remove the metal protective cap which is often placed over the membrane on new test tubes. Consequently, the control arrangement may be constructed to respond to all sensor signals above a given highest permitted pressure level, this level being relatively high, therewith to stop further upward movement of the cylinder 5.

FIG. 2 is a diagram showing the detected sensor pressure as a function of the height position of the cylinder 5 during its upward travel. During a first period, up to $S_1$, no pressure is sensed. At the point $S_1$ the cannula contacts the membrane and penetrates the same. The detected sensor pressure herewith increases radically, although not to the highest permitted pressure level, and then drops immediately the cannula has perforated the membrane. The membrane, however, may also offer a certain degree of resistance to the continued passage of the cannula into the test tube. The sensor 22 will therefore detect a certain amount of pressure in this regard, this pressure being referenced $t_1$. When the position $S_2$ is reached, the cannula 10 is in contact with the bottom of the test tube and the detected sensor pressure will subsequently increase. $S_2$ lies within the range in which the bottom of the test tube can be expected to lie, i.e. the so-called sensitivity range. The control arrangement 21 is therefore constructed to respond within this range to a much lower sensor signal than the highest permitted signal, or alternatively is constructed to respond to pressures which are moderately higher than the sensed pressure $t_1$ and to halt further upward movement of the cylinder 5 in response thereto, and optionally also to lower the cylinder slightly.

The test tubes are often filled with an inert gas, such as nitrogen, in order to prevent the manipulated liquid from being affected by the action of ambient air. In those cases where extremely minute quantities of liquid are concerned, the insertion of the cannula and the delivery of liquid are of no great significance to the pressure in the test tube. It is desirable, however, to be able to use the apparatus for manipulating both minute quantities and slightly larger quantities of liquid. Consequently, there is preferably used a cannula which presents two bores, one for the liquid concerned and one for connection to a source 24 of inert gas. The control arrangement 21 may be connected through a control line to a valve 25 incorporated in the line extending to the source 24, and may be constructed, or programmed, to open the valve during the actual liquid manipulating period, this introduction of the liquid into the cannula being effected subsequent to inserting the cannula into the test tube, and optionally also in conjunction with a liquid control signal dispatched to a liquid control unit (not shown) connected to the hose 14.

When the arrangement illustrated in FIG. 1 is to be used to collect from the tubes 1,2 for analysis purposes, small quantities of liquid which have previously been deposited in said tubes, the pressure prevailing in the source 24 may be higher than that prevailing in the test tube. In this regard the valve 25 may be opened at the precise moment of introducing the liquid located at the bottom of the tube into the cannula 10. This enables the subsequent increase in pressure in the test tube to assist in passing the liquid into the cannula orifice, while simultaneously placing the liquid hose connected to the cannula under a given subpressure.

The embodiment illustrated in FIG. 1 is to be preferred, since it is connected to the liquid transport system by means of a moveable hose. The variations in dynamic and static pressure which occur when the cannula is moved or when the viscosity of the liquid changes alter the volume of the system. This change in volume, which preferably takes place in the flexible parts of the liquid transport system, may quite easily be greater than the volume of liquid to be collected. In the case of existing fraction collectors, this makes it extremely difficult to control the collection of small quantities of liquid in a reliable manner.

In addition, the dynamic forces generated by the movement of the cannula may cause an incompletely developed droplet of liquid to leave the tip of the cannula, therewith jeopardizing the accuracy of the result obtained. Consequently, an advantage is afforded when the cannula is held as stationary as possible, i.e. when the arrangement incorporating the test tubes is arranged to move up and down instead of the cannula assembly.

The concept of the invention, however, can also be applied with existing apparatus equipped with stationary test tube holders and moveable cannula holders. Accordingly, there is illustrated in FIG. 3 a further embodiment of an arrangement according to the invention in which a test tube 26 is placed in a stationary holder 27 and a cannula holder 28 with cannula 29 and sensor 30 is arranged to be raised and lowered in response to instructions from a system control arrangement 31. The system is controlled in accordance with the principles described with reference to FIG. 1.

Many modifications are conceivable within the scope of the invention. If desired, the cannula of the FIG. 1 embodiment can be connected to the liquid transport system by means of rigid and inflexible pipes. The cannula holder may also be made totally immoveable, i.e. so that it is not rotated or twisted between two pipes. This absence of cannula movement minimizes the aforesaid variations in pressure, and therewith also the changes in volume in the liquid transport system which result from such pressure variations. Because it is not necessary to use resilient or flexible pipes, the pipes can be made selectively from materials which will eliminate, either totally or partially, volumetric changes in the pipe systems due to changes in temperature of the liquid or of the surroundings, or to changes in viscosity of the liquid concerned, such changes resulting in pressure changes at constant flow rates, or from materials which enable such volumetric changes to be calculated.

We claim:

1. Apparatus for manipulating a small quantity of liquid, comprising at least one vessel for accommodating said quantity of liquid, a cannula suspension arrangement having a cannula capable of being inserted into said vessel, and a control arrangement which positions the cannula in the bottom of the vessel, the cannula suspension arrangement including a pressure sensor which is coupled to the control arrangement and which acts on the control arrangement when the tip of the cannula is subjected to a force acting axially to the cannula above a given level to stop further insertion of the cannula into the vessel.

2. Apparatus according to claim 1 in which the vessel is provided with a protective membrane over the opening thereof, and in which the control arrangement is arranged to respond to signals from the pressure sensor solely when the cannula suspension arrangement and a vessel holding arrangement are located within a first pre-determined distance range in relation to one another.

3. Apparatus according to claim 2, in which the control arrangement also responds to signals from the sensor which lie outside the aforesaid distance range, these signals having a highest permitted level which is much higher than the level to which the control arrangement responds within said first distance range, therewith to stop further insertion of the cannula into the vessel.

4. Apparatus according to claim 1, in which the control arrangement moves the system vessel and cannula through a short distance in the reverse direction subsequent to stoppage of further insertion of the cannula into the vessel.

5. Apparatus according to claim 1, in which the cannula suspension arrangement is immoveable in the vertical direction, and the vessel is disposed in a holder device capable of being moved vertically in a controlled manner by the control arrangement.

6. Apparatus according to claim 2, incorporating a plurality of vessels, in which the cannula suspension arrangement and/or a vessel holding device is movable substantially horizontally by the control arrangement when the cannula suspension arrangement and the vessel holder device are spaced apart vertically in a second pre-determined distance range, within which the tip of the cannula upon movement in said horizontal direction moves free from contact with any vessel or vessel holding device.

7. Apparatus according to claim 2, in to which a sensor signal level to which the control arrangement is arranged to respond within said first distance range is a pre-determined level above a detected level during an insertion movement sequence, which lies between a detected level outside said first distance range and said first distance range, this latter detected level being high although lower than the highest permitted level.

* * * * *